(12) United States Patent
Hucl

(10) Patent No.: US 9,879,235 B2
(45) Date of Patent: *Jan. 30, 2018

(54) WHEAT PLANTS HAVING INCREASED RESISTANCE TO IMIDAZOLINONE HERBICIDES

(75) Inventor: Pierre Hucl, Saskatoon (CA)

(73) Assignee: University of Saskatchewan, Saskatoon, Saskatchewan (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/401,943

(22) Filed: Feb. 22, 2012

(65) Prior Publication Data

US 2012/0266333 A1  Oct. 18, 2012

Related U.S. Application Data

(62) Division of application No. 12/362,868, filed on Jan. 30, 2009, now Pat. No. 8,124,847, which is a division of application No. 10/486,582, filed as application No. PCT/CA02/01050 on Jul. 10, 2002, now Pat. No. 7,521,599.

(60) Provisional application No. 60/311,180, filed on Aug. 9, 2001.

(51) Int. Cl.
*A01H 5/10* (2006.01)
*C12N 9/10* (2006.01)
*C12N 9/88* (2006.01)
*C12N 15/82* (2006.01)

(52) U.S. Cl.
CPC ............ *C12N 9/1022* (2013.01); *C12N 9/88* (2013.01); *C12N 15/8278* (2013.01)

(58) Field of Classification Search
None
See application file for complete search history.

(56) References Cited

U.S. PATENT DOCUMENTS

| | | | |
|---|---|---|---|
| 4,761,373 A | 8/1988 | Anderson et al. | |
| 5,013,659 A | 5/1991 | Bedbrook et al. | |
| 5,304,732 A | 4/1994 | Anderson et al. | |
| 5,331,107 A | 7/1994 | Anderson et al. | |
| 5,731,180 A | 3/1998 | Dietrich | |
| 5,767,361 A | 6/1998 | Dietrich | |
| 5,853,973 A | 12/1998 | Kakefuda et al. | |
| 5,928,937 A | 7/1999 | Kakefuda et al. | |
| 6,211,438 B1 | 4/2001 | Anderson et al. | |
| 6,211,439 B1 | 4/2001 | Anderson et al. | |
| 6,222,100 B1 | 4/2001 | Anderson et al. | |
| 6,225,105 B1 | 5/2001 | Sathasivan et al. | |
| 6,339,184 B1* | 1/2002 | Smith | 800/276 |
| 6,613,963 B1* | 9/2003 | Gingera et al. | 800/306 |
| 6,696,294 B1 | 2/2004 | Konzak | |
| 7,521,599 B2* | 4/2009 | Hucl | C12N 9/88 435/410 |
| 8,124,847 B2* | 2/2012 | Hucl | C12N 9/88 800/300 |

FOREIGN PATENT DOCUMENTS

| | | |
|---|---|---|
| EP | 0360750 A2 | 3/1990 |
| EP | 0375875 | 7/1990 |
| EP | 0508161 A1 | 10/1992 |
| EP | 0525384 A2 | 2/1993 |
| WO | WO 90/14000 A1 | 11/1990 |
| WO | WO 99/65292 * | 12/1999 |
| WO | WO 00/53763 | 9/2000 |
| WO | 0192512 A2 | 6/2001 |
| WO | WO 02/092820 A1 | 11/2002 |
| WO | WO 03/014356 A2 | 2/2003 |
| WO | WO 03/014357 A1 | 2/2003 |

OTHER PUBLICATIONS

Lee et al 1999, FEBS Letters 452: 341-345.*
Newhouse et al 1992, Plant Physiology 100: 882-886.*
Anderson, Online Nov. 6, 2000, GenBank Accession BF200418.*
Chang et al 1998, Biochemical Journal 333: 765-777.*
Wright et al 1998, Weed Science 46: 13-23.*
Seefeldt et al 1998, Weed Science 46: 632-634.*
J. Andrew Kendig and M.S. DeFelice, "ALS Resistance Cocklebur (*Xanthium strumarium* L.) in Missouri", WSSA Abstracts, vol. 34, Feb. 7-10, 1994, 1994 Meeting of the Weed Science Society of America.
Barrett, M., "Protection of Grass Crops from Sulfonylurea and Imidazolinone Toxicity," Crop Safeners for Herbicides, 1989, pp. 195-220, Academic Press, Inc.
Bernasconi, P., et al., "A Naturally Occurring Point Mutation Confers Broad Range Tolerance to Herbicides That Target Acetolactate Synthase," The Journal of Biological Chemistry, 1995, pp. 17381-17385, vol. 270(29).
Brown, M., et al., "Hydrolytic Activation versus Oxidative Degradation of Assert Herbicide, an Imidazolinone Aryl-carboxylate, in Susceptible Wild Oat versus Tolerant Corn and Wheat," Pesticide Biochemistry and Physiology, 1987, pp. 24-29, vol. 27, Academic Press, Inc.
Chang, A., and R. Duggelby, "Herbicide-resistant Forms of Arabidopsis thaliana Acetohydroxyacid Synthase: Characterization of the Catalytic Properties and Sensitivity to Inhibitors of Four Defined Mutants," Biochemistry 1, 1998, pp. 765-777, vol. 333.
Chong C., and J. Choi, "Amino Acid Residues Conferring Herbicide Tolerance in Tobacco Acetolactate Synthase," Biochemical and Biophysical Research Communications, 2000, pp. 462-467, vol. 279, Academic Press.
Duggleby, R., et al., "Systematic Characterization of Mutations in Yeast Acetohydroxyacid Synthase," Eur. J Biochem., 2003, pp. 2895-2904, vol. 270.

(Continued)

*Primary Examiner* — David H Kruse
(74) *Attorney, Agent, or Firm* — Mintz Levin Cohn Ferris Glovsky and Popeo, P.C.

(57) ABSTRACT

The present invention is directed to wheat plants having increased resistance to an imidazolinone herbicide. More particularly, the present invention includes wheat plants containing one or more IMI nucleic acids such as an Einkorn IMI cultivar. The present invention also includes seeds produced by these wheat plants and methods of controlling weeds in the vicinity of these wheat plants.

29 Claims, 6 Drawing Sheets

(56) References Cited

OTHER PUBLICATIONS

Hattori, J., et al., "Multiple Resistance to Sulfonylureas and Imidazolinones Conferred by an Acetohydroxyacid Synthase Gene with Separate Mutations for Selective Resistance," Molecular Genetics, 1992, pp. 167-173, vol. 232.

Lee, Y., et al., "Effect of Mutagenesis at Serine 653 of *Arabidopsis thaliana* Acetohydroxyacid Synthase on the Sensitivity to Imidazolinone and Sulfonylurea Herbicides," FEBS Letters, 1999, pp. 341-345, vol. 452, Federation of European Biochemical Societies.

Mourad, G., et al., "Isolation and Genetic Analysis of a Triazolopyrimidine-Resistant Mutant of *Arabidopsis*," J Heredity, 1993, pp. 91-96, vol. 84.

Newhouse, K., et al., "Mutations in corn (*Zea mays* L.) Conferring Resistance to Imidazolinone Herbicides," Theor. Appl. Genet., 1991, pp. 65-70, vol. 83, Springer-Verlag.

Newhouse, K., et al., "Tolerance to Imidazolinone Herbicides in Wheat," Plant Physiology, 1992, pp. 882-886, vol. 100.

Odell, et al., "Comparison of Increased Expression of Wild-Type and Herbicide Resistant Acetolactate Synthase Genes in Transgenic Plants, and Indication of Posttranscriptional Limitation on Enzyme Activity," Plant Physiol., (1990), pp. 1647-1654, vol. 94.

Ott, K., et al., "Rational Molecular Design and Genetic Engineering of Herbicide Resistant Crops by Structure Modeling and Site-directed Mutagenesis of Acetohydroxyacid Synthase," J Mol. Biol., 1996, pp. 359-368, vol. 263, Academic Press Limited.

Repellin, A., et al., "Genetic Enrichment of Cereal Crops via Alien Gene Transfer: New Challenges," Plant Cell, Tissue and Organ Culture, 2001, pp. 159-183, vol. 64.

Sathasivan, K., et al., "Nucleotide Sequence of a Mutant Acetolactate synthase Gene from an Imidaziolinone-resistant *Arabidopsis thaliana* var. Columbia," Nudeic Acids Research, 1990, pp. 2188, vol. 18(8), Oxford University Press.

Sathasivan, K., et al., "Molecular Basis of Imidazolinone Herbicide Resistance in *Arabidopsis thaliana* var Columbia," Plant Physiol., 1991, pp. 1044-1050, vol. 97.

Paul R. Schmitzer et al., "Lack of Cross-Resistance of Imazaquin-Resistant Xanthiu strumarium Acetolactate Synthase to Flumetsulam and Chlorimuron", Plant Physiol., vol. 103, 1993, pp. 281-283.

Sebastian, S., et al., "Semidominant Soybean Mutation for Resistance to Sulfonylurea Herbicides," Crop. Sci., 1989, pp. 1403-1408, vol. 29.

Shaner, D., et al., "Imidazolinone-Resistant Crops: Selection, Characterization, and Management," Herbicide-Resistant Crops: Agricultural, Environmental, Economic, 1996, pp. 143-157.

Shaner, D. and P.A. Robson, "Absorption, Translocation, and Metabolism of AC 25 214 in Soybean (Glycine max), Common Cocklebur (Xanthium Strumarium), and Velvetlea (Abutilon theo hrasti)," Weed Sci., 1985, pp. 469-471, vol. 33.

Shaner, D., et al., "Imidazolinones: Potent Inhibitors of Acetohydroxyacid Synthase," Plant Physiol., 1984, pp. 545-546, vol. 76.

Singh, B.K., "Biosynthesis of Valine, Leucine and Isoleucine," Plant Amino Acids, 1999, pp. 227-247, Marcel Dekker Inc., New York, NY.

Swanson, E., et al., "Microspore Mutagenesis and Selection: Canola Plants with Field Tolerance to the Imidazolinones," Theor. Appl. Genet., 1989, pp. 525-530, vol. 78, Springer-Verlag.

White, A., et al., "Common sunflower resistance to acetolactate synthase-inhibiting herbicides," Weed Science, 2002, pp. 432-437, vol. 50.

Wright, T.R. and D. Penner, "Cell Selection and Inheritance of Imidazolinone Resistance in Sugarbeet (*Beta vulgaris*)," Theor. Appl. Genet., 1998, pp. 612-620, vol. 96, Springer-Verlag.

GenBank Accession No. BE417248. Created Jul. 24, 2000.

GenBank Accession No. BF200418. Created Nov. 6, 2000.

EMBL Accession No. AF059600. Created Apr. 27, 1998.

* cited by examiner

Figure 1

Partial cDNA sequence of Einkorn IMI3 (SEQ ID NO:1)

GATGGTAGTTTCCTCATGAACATTCAGGAGTTGGCGTTGATCCGTATTGAGAACCTCCCAGTGAAGGTGA
TGATATTGAACAACCAGCATCTGGGAATGGTGGTGCAGTGGGAGGATAGGTTTTACAAGGCCAACCGGGCA
CACACATACCTTGGCAACCCAGAAAATGAGAGTGAGATATATCCAGATTTTGTGACGATTGCTAAAGGATT
CAACGTTCCGGCAGTTCGTGTGACGAAGAAGAGCGAAGTCACTGCAGCAATCAAGAAGATGCTTGAGACCC
CAGGGCCATACTTGTTGGATATCATTGTCCCGCATCAGGAGCACGTGCTGCCTATGATCCCAAACGGAGGT
GCTTTTAAGGACATGA

Figure 2

```
                                                                    400
3_end_Einkorn  (SEQ ID NO:2)  (381)            GATGGTAGTTTCCTCATGAA
          EM2  (SEQ ID NO:1)    (1)            GATGGTAGTTTCCTCATGAA
    Consensus  (SEQ ID NO:3)  (381)            GATGGTAGTTTCCTCATGAA
                                401                                 450
3_end_Einkorn                 (401) CATTCAGGAGTTGGCGTTGATCCGTATTGAGAACCTCCCAGTGAAGGTGA
          EM2                  (31) CATTCAGGAGTTGGCGTTGATCCGTATTGAGAACCTCCCAGTGAAGGTGA
    Consensus                 (401) CATTCAGGAGTTGGCGTTGATCCGTATTGAGAACCTCCCAGTGAAGGTGA
                                451                                 500
3_end_Einkorn                 (451) TGATATTGAACAACCAGCATCTGGGAATGGTGGTGCAGTGGGAGGATAGG
          EM2                  (81) TGATATTGAACAACCAGCATCTGGGAATGGTGGTGCAGTGGGAGGATAGG
    Consensus                 (451) TGATATTGAACAACCAGCATCTGGGAATGGTGGTGCAGTGGGAGGATAGG
                                501                                 550
3_end_Einkorn                 (501) TTTTACAAGGCCAACCGGGCACACACATACCTTGGCAACCCAGAAAATGA
          EM2                 (131) TTTTACAAGGCCAACCGGGCACACACATACCTTGGCAACCCAGAAAATGA
    Consensus                 (501) TTTTACAAGGCCAACCGGGCACACACATACCTTGGCAACCCAGAAAATGA
                                551                                 600
3_end_Einkorn                 (551) GAGTGAGATATATCCAGATTTTGTGACGATTGCTAAAGGATTCAACGTTC
          EM2                 (181) GAGTGAGATATATCCAGATTTTGTGACGATTGCTAAAGGATTCAACGTTC
    Consensus                 (551) GAGTGAGATATATCCAGATTTTGTGACGATTGCTAAAGGATTCAACGTTC
                                601                                 650
3_end_Einkorn                 (601) CGGCAGTTCGTGTGACGAAGAAGAGCGAAGTCACTGCAGCAATCAAGAAG
          EM2                 (231) CGGCAGTTCGTGTGACGAAGAAGAGCGAAGTCACTGCAGCAATCAAGAAG
    Consensus                 (601) CGGCAGTTCGTGTGACGAAGAAGAGCGAAGTCACTGCAGCAATCAAGAAG
                                651                                 700
3_end_Einkorn                 (651) ATGCTTGAGACCCCAGGGCCATACTTGTTGGATATCATTGTCCCGCATCA
          EM2                 (281) ATGCTTGAGACCCCAGGGCCATACTTGTTGGATATCATTGTCCCGCATCA
    Consensus                 (651) ATGCTTGAGACCCCAGGGCCATACTTGTTGGATATCATTGTCCCGCATCA
                                701                                 750
3_end_Einkorn                 (701) GGAGCACGTGCTGCCTATGATCCCAAGCGGAGGTGCTTTTAAGGACATGA
          EM2                 (331) GGAGCACGTGCTGCCTATGATCCCAAACGGAGGTGCTTTTAAGGACATGA
    Consensus                 (701) GGAGCACGTGCTGCCTATGATCCCAA CGGAGGTGCTTTTAAGGACATGA
```

Figure 4

| Code | Description |
|---|---|
| EM2 | Doubled haploid derived line from P00.45 (see Example 2) |
| 11A | A hexaploid wheat line containing the homozygous IMI mutation 11A, shown to be non-allelic with both the 15A mutations and the FS4 mutation |
| EM2FS4 | Doubled haploid derived line containing both the EM2 mutation from einkorn wheat introgressed into a hexaploid wheat background and the FS4 mutation in hexaploid wheat |
| 15A | A hexaploid wheat line containing the homozygous IMI mutations 15A, shown to have two independent IMI tolerance genes, one of which was allelic to the FS4 mutation |
| FS4 | A hexaploid wheat line containing the homozygous IMI mutation FS4, a single locus, located on the D genome (Jim Anderson, personal communication) |
| Teal | A hexaploid wheat susceptible to application of imazamox |

Figure 5

| Table Line# | Cross | Gen | Observed Toler. | Susc. | Ratio | Expected Toler. | Susc. | p |
|---|---|---|---|---|---|---|---|---|
| 1 | 11A/Teal | F2 | 505 | 189 | 3:1 | 521 | 174 | 0.1742 |
| 2 | 15A/Teal | F2 | 893 | 74 | 15:1 | 907 | 60 | 0.0716 |
| 3 | EM2/15A | F2 | 1940 | 0 | | | | |
| 4 | 15A/FS4 | F2 | 410 | 0 | | | | |
| 5 | EM2+FS4/15A | F2 | 1134 | 0 | | | | |
| 6 | EM2/11A | F2 | 1331 | 100 | 15:1 | 1342 | 89 | 0.2300 |
| 7 | EM2/FS4 | F2 | 1192 | 72 | 15:1 | 1185 | 79 | 0.4160 |
| 8 | EM2+FS4/11A | F2 | 622 | 16 | 63:1 | 628 | 10 | 0.0580 |
| 9 | 11A/FS4 | F2 | 688 | 47 | 15:1 | 689 | 46 | 0.8714 |
| 10 | 11A/15A | F2 | 600 | 14 | 63:1 | 604 | 10 | 0.1516 |

Figure 6

| | Einkorn check | | EM2 | |
|---|---|---|---|---|
| | imazamox, g/ha | | imazamox, g/ha | |
| 1998 | 0 | 40 | 0 | 40 |
| Yield (kg/ha) | 3011 | 0 | 3792 | 3494 |
| Heading (days) | 52 | 0 | 52 | 53 |
| Maturity (days) | 79 | 0 | 79 | 79 |
| Height (cm) | 85 | 0 | 85 | 85 |
| 1999 | | | | |
| Yield (kg/ha) | 2349 | 0 | 2687 | 3219 |
| Heading (days) | 63 | 0 | 62 | 62 |
| Maturity (days) | 110 | 0 | 110 | 110 |
| Height (cm) | 109 | 0 | 106 | 108 |
| 2000 | | | | |
| Yield (kg/ha) | 2238 | 0 | 2676 | 2684 |

Figure 7

|  | g ai/ha | %Injury at three time points (DAT=days after treatment at 3-4 leaf stage) | | | | | |
|---|---|---|---|---|---|---|---|
|  |  | EM2 | | | Einkorn Check | | |
|  |  | 16 DAT | 41 DAT | 78 DAT | 16 DAT | 41 DAT | 78 DAT |
| 1999 1 Loc | 0 | 0.0 | 0.0 | 0.0 | 0.0 | 0.0 | 0.0 |
|  | 15 | 2.5 | 0.3 | 0.0 | 93.8 | 100.0 | 97.3 |
|  | 30 | 2.5 | 1.3 | 0.0 | 96.0 | 99.5 | 99.3 |
|  | 60 | 7.5 | 2.5 | 0.0 | 97.0 | 100.0 | 99.5 |
|  |  | EM2 | | | Einkorn Check | | |
|  |  | 18 DAT | 44 DAT | 73 DAT | 18 DAT | 44 DAT | 73 DAT |
| 2000 2 Loc Ave | 0 | 0.0 | 0.0 | 0.0 | 0.0 | 0.0 | 0.0 |
|  | 15 | 0.0 | 0.0 | 0.0 | 93.1 | 96.9 | 98.1 |
|  | 30 | 0.0 | 0.0 | 0.0 | 53.0 | 97.4 | 99.4 |
|  | 60 | 0.0 | 0.0 | 0.0 | 97.5 | 99.5 | 100.0 |

Figure 8

|            | g/ha Imazamox |           |          |           |
|------------|---------------|-----------|----------|-----------|
|            | 200           |           | 600      |           |
| Genotype   | %Injured      | %No Injury| %Injured | %No Injury|
| BW755 (FS4)    | 100 | 0   | 100 | 0  |
| Teal 15A (2 gene) | 0   | 100 | 100 | 0  |
| EM2/FS4 (2 gene)  | 0   | 100 | 100 | 0  |
| 15A/11A (3 gene)  | 33  | 67  | 48  | 52 |

WHEAT PLANTS HAVING INCREASED RESISTANCE TO IMIDAZOLINONE HERBICIDES

This application is a divisional of U.S. patent application Ser. No. 12/362,868, filed Jan. 30, 2009, now U.S. Pat. No. 8,124,847, to be issued on Feb. 28, 2012, which is a divisional of U.S. patent application Ser. No. 10/486,582, filed Jul. 19, 2004, now U.S. Pat. No. 7, 521, 599 issued on Apr. 21, 2009, which is the U.S. National Stage of International Application PCT/CA02/01050, filed Jul. 10, 2002, which published in English on Feb. 20, 2003 and designates the U.S., which claims the priority benefit of U.S. Provisional Patent Application Ser. No. 60/311,180 filed Aug. 9, 2001; all of which are hereby incorporated herein in their entirety by reference.

FIELD OF THE INVENTION

The present invention relates in general to plants having an increased resistance to imidazolinone herbicides. More specifically, the present invention relates to wheat plants obtained by mutagenesis and cross-breeding and transformation that have an increased resistance to imidazolinone herbicides.

BACKGROUND OF THE INVENTION

Acetohydroxyacid synthase (AHAS; EC 4.1.3.18) is the first enzyme that catalyzes the biochemical synthesis of the branched chain amino acids valine, leucine and isoleucine (Singh B. K., 1999 Biosynthesis of valine, leucine and isoleucine in: Singh B. K. (Ed) Plant amino acids. Marcel Dekker Inc. New York, N.Y. Pg 227-247). AHAS is the site of action of four structurally diverse herbicide families including the sulfonylureas (LaRossa R A and Falco S C, 1984 Trends Biotechnol. 2:158-161), the imidazolinones (Shaner et al., 1984 Plant Physiol. 76:545-546), the triazolopyrimidines (Subramanian and Gerwick, 1989 Inhibition of acetolactate synthase by triazolopyrimidines in (ed) Whitaker J R, Sonnet P E Biocatalysis in agricultural biotechnology. ACS Symposium Series, American Chemical Society. Washington, D.C. Pg 277-288), and the pyrimidyloxybenzoates (Subramanian et al., 1990 Plant Physiol 94: 239-244.). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluazasulfuron, imazosulfuron, pyrazosulfuron ethyl and halosulfuron.

Due to their high effectiveness and low-toxicity, imidazolinone herbicides are favored for application by spraying over the top of a wide area of vegetation. The ability to spray an herbicide over the top of a wide range of vegetation decreases the costs associated with plantation establishment and maintenance and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson, 1985 Weed Sci. 33:469-471). Other crops such as corn (Newhouse et al., 1992 Plant Physiol. 100:882-886) and rice (Barrette et al., 1989 Crop Safeners for Herbicides, Academic Press New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al., 1984 Plant Physiol. 76:545-546; Brown et al., 1987 Pestic. Biochem. Physiol. 27:24-29). Other plant physiological differences such as absorption and translocation also play an important role in sensitivity (Shaner and Robinson, 1985 Weed Sci. 33:469-471).

Crop cultivars resistant to imidazolinones, sulfonylureas and triazolopyrimidines have been successfully produced using seed, microspore, pollen, and callus mutagenesis in *Zea mays, Arabidopsis thaliana, Brassica napus, Glycine max*, and *Nicotiana tabacum* (Sebastian, et al., 1989 Crop Sci. 29:1403-1408; Swanson et al., 1989 Theor. Appl. Genet. 78:525-530; Newhouse et al., 1991 Theor. Appl. Genet. 83:65-70; Sathasivan et al., 1991 Plant Physiol. 97:1044-1050; Mourand et al., 1993 J. Heredity 84: 91-96). In all cases, a single, partially dominant nuclear gene conferred resistance. Four imidazolinone resistant wheat plants were also previously isolated following seed mutagenesis of *Triticum aestivum* L. cv Fidel (Newhouse et al., 1992 Plant Physiol. 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al., 1992 Plant Physiol. 100:882-886).

Computer-based modeling of the three dimensional conformation of the AHAS-inhibitor complex predicts several amino acids in the proposed inhibitor binding pocket as sites where induced mutations would likely confer selective resistance to imidazolinones (Ott et al., 1996 J. Mol. Biol. 263:359-368) Wheat plants produced with some of these rationally designed mutations in the proposed binding sites of the AHAS enzyme have in fact exhibited specific resistance to a single class of herbicides (Ott et al., 1996 J. Mol. Biol. 263:359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone resistant corn lines. U.S. Pat. No. 5,013,659 discloses plants exhibiting herbicide resistance possessing mutations in at least one amino acid in one or more conserved regions. The mutations described therein encode either cross-resistance for imidazolinones and sulfonylureas or sulfonylurea-specific resistance, but imidazolinone-specific resistance is not described. Additionally, U.S. Pat. Nos. 5,731,180 and 5,767,361 discuss an isolated gene having a single amino acid substitution in a wild-type monocot AHAS amino acid sequence that results in imidazolinone-specific resistance.

To date, the prior art has not described imidazolinone resistant wheat plants containing more than one altered AHAS gene. Nor has the prior art described imidazolinone resistant wheat plants containing mutations on genomes other than the genome from which the FS-4 gene is derived. Therefore, what is needed in the art is the identification of imidazolinone resistance genes from additional genomes. What are also needed in the art are wheat plants having increased resistance to herbicides such as imidazolinone and containing more than one altered AHAS gene. Also needed are methods for controlling weed growth in the vicinity of such wheat plants. These compositions and methods would allow for the use of spray over techniques when applying herbicides to areas containing wheat plants.

SUMMARY OF THE INVENTION

The present invention provides wheat plants comprising IMI nucleic acids, wherein the wheat plant has increased resistance to an imidazolinone herbicide as compared to a wild-type variety of the plant. The wheat plants can contain one, two, three or more IMI nucleic acids. In one embodiment, the wheat plant comprises multiple IMI nucleic acids located on different genomes. Preferably, the IMI nucleic acids encode proteins comprising a mutation in a conserved amino acid sequence selected from the group consisting of a Domain A; a Domain B, a Domain C, a Domain D and a Domain E. More preferably, the mutation is in a conserved Domain E or a conserved Domain C. Also provided are plant parts and plant seeds derived from the wheat plants described herein. In another embodiment, the wheat plant comprises an IMI nucleic acid that is not an Imi1 nucleic acid. The IMI nucleic acid can be an Imi2 or Imi3 nucleic acid, for example.

The IMI nucleic acids of the present invention can comprise a nucleotide sequence selected from the group consisting of: a polynucleotide of SEQ ID NO:1; a polynucleotide comprising at least 60 consecutive nucleotides of SEQ ID NO:1; and a polynucleotide complementary to SEQ ID NO:1.

The plants of the present invention can be transgenic or non-transgenic. Examples of non-transgenic wheat plants having increased resistance to imidazolinone herbicides include a wheat plant having an ATCC Patent Deposit Designation Number PTA-4113; or a mutant, recombinant, or genetically engineered derivative of the plant with ATCC Patent Deposit Designation Number PTA-4113; or of any progeny of the plant with ATCC Patent Deposit Designation Number PTA-4113; or a plant that is a progeny of any of these plants.

In addition to the compositions of the present invention, several methods are provided. Described herein are methods of modifying a plant's tolerance to an imidazolinone herbicide comprising modifying the expression of an IMI nucleic acid in the plant. Also described are methods of producing a transgenic plant having increased tolerance to an imidazolinone herbicide comprising, transforming a plant cell with an expression vector comprising one or more IMI nucleic acids and generating the plant from the plant cell. The invention further includes a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant and wherein the plant comprises one or more IMI nucleic acids. In some preferred embodiments of these methods, the plants comprise multiple IMI nucleic acids that are located on different wheat genomes.

BRIEF DESCRIPTION OF THE DRAWINGS

FIG. 1 shows the partial cDNA sequence of Einkorn IMI3 (SEQ ID NO:1) with the nucleotide change from the wild type Als sequence underlined.

FIG. 2 shows the partial cDNA sequence of Einkorn IMI3 as compared to a wild type Einkorn sequence (SEQ NO:2) and a consensus sequence (SEQ ID NO:3).

FIG. 4 is a table showing parental wheat lines used to determine allelic relationships among IMI genes.

FIG. 5 is a table showing F2 segregation data demonstrating the location of the EM2 mutation on the A genome.

FIG. 6 is a table showing various agronomic characteristics that could be affected by herbicide injury in both Einkorn control and EM2 plants.

FIG. 7 is a table showing the evaluation of an Einkorn control and EM2 plants for overall crop injury at three rates of imazamox.

FIG. 8 is a table showing increased resistance to imidazolinone herbicides in wheat cultivars upon stacking of IMI nucleic acids.

DETAILED DESCRIPTION

Figure 3:
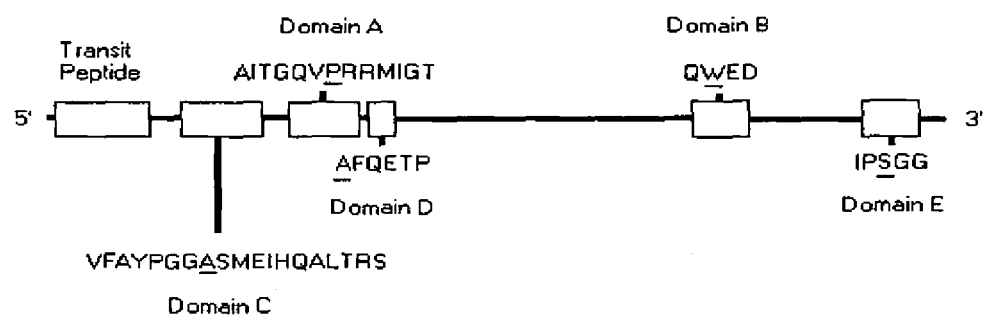
FIG. 3 is a schematic representation of the conserved amino acid sequences in the AHAS genes implicated in resistance to various AHAS inhibitors. The specific amino acid site responsible for resistance is indicated by an underline. (Modified from Devine, M. D. and Eberlein, C. V., 1997 Physiological, biochemical and molecular aspects of herbicide resistance based on altered target sites in Herbicide Activity: Toxicity, Biochemistry, and Molecular Biology, IOS Press Amsterdam, p. 159-185).

The present invention is directed to wheat plants, wheat plant parts and wheat plant cells having increased resistance to imidazolinone herbicides. The present invention also includes seeds produced by the wheat plants described herein and methods for controlling weeds in the vicinity of the wheat plants described herein. It is to be understood that as used in the specification and in the claims, "a" or "an" can mean one or more, depending upon the context in which it is used. Thus, for example, reference to "a cell" can mean that at least one cell can be utilized.

As used herein, the term "wheat plant" refers to a plant that is a member of the *Triticum* genus. The wheat plants of the present invention can be members of a *Triticum* genus including, but not limited to, *T. aestivum, T. turgidum, T. timopheevii, T. monococcum, T. zhukovskyi* and *T. urartu* and hybrids thereof. Examples of *T. aestivum* subspecies included within the present invention are *aestivum* (common wheat), *compactum* (club wheat), *macha* (macha wheat), *vavilovi* (vavilovi wheat), *spelta* and *sphaecrococcum* (shot wheat). Examples of *T. turgidum* subspecies included within the present invention are *turgidum, carthlicum, dicoccon, durum, paleocolchicum, polonicum, turanicum* and *dicoccoides*. Examples of *T. monococcum* subspecies included within the present invention are *monococcum* (einkorn) and *aegilopoides*. In one embodiment of the present invention, the wheat plant is a member of the *Triticum monococcum* species, and more particularly, the Einkorn accession.

The term "wheat plant" is intended to encompass wheat plants at any stage of maturity or development as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts and the like. The present invention also includes seeds produced by the wheat plants of the present invention. In one embodiment, the seeds are true breeding for an increased resistance to an imidazolinone herbicide as compared to a wild type variety of the wheat plant seed.

The present invention describes a wheat plant comprising one or more IMI nucleic acids, wherein the wheat plant has increased resistance to an imidazolinone herbicide as compared to a wild-type variety of the plant. As used herein, the term "IMI nucleic acid" refers to a nucleic acid that is mutated from an AHAS nucleic acid in a wild type wheat plant that confers increased imidazolinone resistance to a plant in which it is transcribed. In one embodiment, the wheat plant comprises multiple IMI nucleic acids. As used when describing the IMI nucleic acids, the term "multiple" refers to IMI nucleic acids that have different nucleotide sequences and does not refer to a mere increase in number of the same IMI nucleic acid. For example, the IMI nucleic acids can be different due to the fact that they are derived from or located on different wheat genomes.

It is possible for the wheat plants of the present invention to have multiple IMI nucleic acids from different genomes since these plants can contain more than one genome. For example, a *Triticum aestivum* wheat plant contains three genomes sometimes referred to as the A, B and D genomes. Because AHAS is a required metabolic enzyme, it is assumed that each genome has at least one gene coding for the AHAS enzyme, commonly seen with other metabolic enzymes in hexaploid wheat that have been mapped. The AHAS nucleic acid on each genome can, and usually does, differ in its nucleotide sequence from an AHAS nucleic acid on another genome. One of skill in the art can determine the genome of origin of each AHAS nucleic acid through genetic crossing and/or either sequencing methods or exonuclease digestion methods known to those of skill in the art. For the purposes of this invention, IMI nucleic acids derived from one of the A, B or D genomes are distinguished and designated as Imi1, Imi2 or Imi3 nucleic acids. It is not stated herein that any particular Imi nucleic acid class correlates with any particular A, B or D genome. For example, it is not stated herein that the Imi1 nucleic acids correlate to A genome nucleic acids, that Imi2 nucleic acids correlate to B genome nucleic acids, etc. The Imi1, Imi2 and Imi3 designations merely indicate that the IMI nucleic acids within each such class do not segregate independently, whereas two IMI nucleic acids from different classes do segregate independently and may therefore be derived from different wheat genomes.

The Imi1 class of nucleic acids includes the FS-4 gene as described by Newhouse et al. (1992 Plant Physiol. 100:882-886). The Imi3 class of nucleic acids includes the Einkorn IMI3 gene described below. Each Imi class can include members from different wheat species. Therefore, each Imi class includes IMI nucleic acids that differ in their nucleotide sequence but that are nevertheless designated as originating from, or being located on, the same wheat genome using inheritance studies as known to those of ordinary skill in the art.

Accordingly, the present invention includes a wheat plant comprising one or more IMI nucleic acids, wherein the wheat plant has increased resistance to an imidazolinone herbicide as compared to a wild-type variety of the plant and wherein the one or more IMI nucleic acids are selected from a group consisting of an Imi1, Imi2 and Imi3 nucleic acid. In one embodiment, the plant comprises an Imi3 nucleic acid. In a preferred embodiment, the Imi3 nucleic acid comprises the polynucleotide sequence shown in SEQ ID NO:1. In another embodiment, the plant comprises an Imi1 or an Imi2 nucleic acid.

As used herein with regard to nucleic acids, the term "from" refers to a nucleic acid "located on" or "derived from" a particular genome. The term "located on" refers to a nucleic acid contained within that particular genome. As also used herein with regard to a genome, the term "derived from" refers to a nucleic acid that has been removed or isolated from that genome. The term "isolated" is defined in more detail below.

In another embodiment, the wheat plant comprises an IMI nucleic acid, wherein the nucleic acid is a non-Imi1 nucleic acid. The term "non-Imi1", refers to an IMI nucleic acid that is not a member of the Imi1 class as described above. One example of non-Imi1 nucleic acid is the polynucleotide sequence shown in SEQ ID NO:1. Accordingly, in a preferred embodiment, the wheat plant comprises an IMI nucleic acid comprising the polynucleotide sequence shown in SEQ ID NO:1.

The present invention includes wheat plants comprising one, two, three or more IMI nucleic acids, wherein the wheat plant has increased resistance to an imidazolinone herbicide as compared to a wild-type variety of the plant. The IMI nucleic acids can comprise a nucleotide sequence selected from the group consisting of a polynucleotide of SEQ ID NO:1; a polynucleotide comprising at least 60 consecutive nucleotides of SEQ ID NO:1; and a polynucleotide complementary to SEQ ID NO:1.

The imidazolinone herbicide can be selected from, but is not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, or a mixture of two or more of the aforementioned herbicides, for example, imazapyr/imazamox (ODYSSEY®). More specifically, the imidazolinone herbicide can he selected from, but is not limited to, 2-(4-isopropyl-4-methyl-5-oxo-2-imidiazolin-2-yl)-nicotinic acid, 2-(4-isopropyl)-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate. The use of 5-ethyl-2-(4-isopropyl-4-methyl-5-oxo-2-imidazolin-2-yl)-nicotinic acid and 2-(4-isopropyl-4-methyl-5-oxo-2-imidazolin-2-yl)-5-(methoxymethyl)-nicotinic acid is preferred. The use of 2-(4-isopropyl-4-methyl-5-oxo-2-imidazolin-2-yl)-5-(methoxymethyl)-nicotinic acid is particularly preferred.

In one embodiment, the wheat plant comprises two IMI nucleic acids, wherein the nucleic acids are derived from or located on different wheat genomes. Preferably, one of the two nucleic acids is an Imi3 nucleic acid. More preferably, the Imi3 nucleic acid comprises the polynucleotide sequence of SEQ ID NO:1. In another embodiment, the wheat plant comprises one IMI nucleic acid, wherein the nucleic acid comprises the polynucleotide sequence of SEQ ID NO:1. In yet another embodiment, the wheat plant comprises three or more IMI nucleic acids wherein each nucleic acid is from a different genome. Preferably, at least one of the three IMI nucleic acids comprises a polynucleotide sequence as shown in SEQ ID NO:1.

In a preferred embodiment of the present invention, the one or more IMI nucleic acids contained within the plant encode an amino acid sequence comprising a mutation in a domain that is conserved among several AHAS proteins. These conserved domains are referred to herein as Domain A, Domain B, Domain C, Domain D and Domain E. FIG. 2 shows the general location of each domain in an AHAS protein. Domain A contains the amino acid sequence AIT-GQVPRRMIGT (SEQ ID NO:4). Domain B contains the amino acid sequence QWED (SEQ ID NO:5). Domain C contains the amino acid sequence VFAYPGGASMEI-HQALTRS (SEQ ID NO:6). Domain D contains the amino acid sequence AFQETP (SEQ ID NO:7). Domain E contains the amino acid sequence IPSGG (SEQ ID NO:8). The present invention also contemplates that there may be slight variations in the conserved domains, for example, in cockleberry plants, the serine residue in Domain E is replaced by an alanine residue.

Accordingly, the present invention includes a wheat plant comprising an IMI nucleic acid that encodes an amino acid sequence having a mutation in a conserved domain selected from the group consisting of a Domain A, a Domain B, a Domain C, a Domain D and a Domain E. In one embodiment, the wheat plant comprises an IMI nucleic acid that encodes an amino acid sequence having a mutation in a Domain E. In further preferred embodiments, the mutations in the conserved domains occur at the locations indicated by the following underlining: AITGQVPRRMIGT (SEQ ID NO:4); QWED (SEQ ID NO:5); VFAYPGG ASMEIHQALTRS (SEQ ID NO:6); AFQETP (SEQ ID NO:7) and IPSGG (SEQ ID NO:8). One preferred substitution is asparagine for serine in Domain E (SEQ ID NO:8).

The wheat plants described herein can be either transgenic wheat plants or non-transgenic wheat plants. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding. Plants containing mutations arising due to non-spontaneous mutagenesis and selective breeding are referred to herein as non-transgenic plants and are included in the present invention. In embodiments wherein the wheat plant is transgenic and comprises multiple IMI nucleic acids, the nucleic acids can be derived from different genomes or from the same genome. Alternatively, in embodiments wherein the wheat plant is non-transgenic and comprises multiple IMI nucleic acids, the nucleic acids are located on different genomes or on the same genome.

An example of a non-transgenic wheat plant cultivar comprising one IMI nucleic acid is the plant cultivar deposited with the ATCC under Patent Deposit Designation Number PTA-4113 and designated herein as the Einkorn IMI wheat cultivar. The Einkorn IMI wheat cultivar contains an Imi3 nucleic acid. The partial nucleotide sequence corresponding to the Einkorn IMI gene is shown in SEQ ID NO:1.

A deposit of 2500 seeds of the Einkorn IMI wheat cultivars was made with the American Type Culture Collection, Manassas, Va. on Mar. 4, 2002. The deposit was made in accordance with the terms and provisions of the Budapest Treaty relating to the deposit of microorganisms. The deposit was made for a term of at least thirty years and at least five years after the most recent request for the furnishing of a sample of the deposit is received by the ATCC. The deposited seeds were accorded Patent Deposit Designation Number PTA-4113.

The present invention includes the wheat plant having a Patent Deposit Designation Number PTA-4113; a mutant, recombinant, or genetically engineered derivative of the plant with Patent Deposit Designation Number PTA-4113; any progeny of the plant with Patent Deposit Designation Number PTA-4113; and a plant that is the progeny of any of these plants. In a preferred embodiment, the wheat plant of the present invention additionally has the herbicide resistance characteristics of the plant with Patent Deposit Designation Number PTA-4113.

Also included in the present invention are hybrids of the Einkorn IMI wheat cultivars described herein and another wheat cultivar. The other wheat cultivar includes, but is not limited to, T. aestivum L. cv Fidel and any wheat cultivar harboring a mutant gene FS-1, FS-2, FS-3 or FS-4. and another wheat cultivar including, but not limited to, T. aestivum L. cv Fidel, and more particularly, those Fidel cultivars harboring mutant genes FS1, FS2, FS3 or FS4. (See U.S. Pat. No. 6,339,184 and U.S. patent application Ser. No. 08/474,832).

The terms "cultivar" and "variety" refer to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. In the present invention, the trait arises from a mutation in an AHAS gene of the wheat plant or seed.

In addition to wheat plants, the present invention encompasses isolated IMI proteins and nucleic acids. The nucleic acids comprise a polynucleotide selected from the group consisting of a polynucleotide of SEQ. ID NO:1; a polynucleotide comprising at least 60 consecutive nucleotides of SEQ ID NO:1; and a polynucleotide complementary to SEQ ID NO:1. In a preferred embodiment, the IMI nucleic acid comprises a polynucleotide sequence of SEQ ID NO:1.

The term "AHAS protein" refers to an acetohydroxyacid synthase protein and the term "IMI protein" refers to any AHAS protein that is mutated from a wild type AHAS protein and that confers increased imidazolinone resistance to a plant, plant cell, plant part, plant seed or plant tissue when it is expressed therein. In a preferred embodiment, the IMI protein comprises a polypeptide encoded by the polynucleotide of SEQ ID NO:1. As also used herein, the terms "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated IMI nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Triticum monococcum* cell). A nucleic acid is also considered isolated if it has been altered by human intervention, or placed in a locus or location that is not its natural site, or if it is introduced into a cell by agroinfection or biolistics. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule containing a nucleotide sequence of SEQ ID NO:1 or a portion thereof, can be isolated using standard molecular biology techniques and the sequence information provided herein. For example, a *T. monococcum* IMI cDNA can be isolated from a *T. monococcum* library using all or a portion of the sequence of SEQ ID NO:1. Moreover, a nucleic acid molecule encompassing all or a portion of SEQ ID NO:1 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an IMI nucleotide sequence can be prepared by standard synthetic techniques, e.g., using an automated DNA synthesizer.

The IMI nucleic acids of the present invention can comprise sequences encoding an IMI protein (i.e., "coding regions"), as well as 5' untranslated sequences and 3' untranslated sequences. Alternatively, the nucleic acid molecules of the present invention can comprise only the coding regions of an IMI gene, or can contain whole genomic fragments isolated from genomic DNA. A coding region of these sequences is indicated as an "ORF position". Moreover, the nucleic acid molecule of the invention can comprise a portion of a coding region of an IMI gene, for example, a fragment that can be used as a probe or primer. The nucleotide sequences determined from the cloning of the IMI genes from *T. monococcum* allow for the generation of probes and primers designed for use in identifying and/or cloning IMI homologs in other cell types and organisms, as well as IMI homologs from other wheat plants and related species. The portion of the coding region can also encode a biologically active fragment of an IMI protein.

As used herein, the term "biologically active portion of" an IMI protein is intended to include a portion, e.g., a domain/motif, of an IMI protein that, when produced in a plant increases the plant's resistance to an imidazolinone herbicide as compared to a wild-type variety of the plant. Methods for quantitating increased resistance to imidazolinone herbicides are provided in the Examples below. Biologically active portions of an M protein include peptides encoded by polynucleotide sequences comprising SEQ ID NO:1 which include fewer amino acids than a full length IMI protein and impart increased resistance to an imidazolinone herbicide upon expression in a plant. Typically, biologically active portions (e.g., peptides which are, for example, 5, 10, 15, 20, 30, 35, 36, 37, 38, 39, 40, 50, 100 or more amino acids in length) comprise a domain or motif with at least one activity of an IMI protein. Moreover, other biologically active portions in which other regions of the polypeptide are deleted, can be prepared by recombinant techniques and evaluated for one or more of the activities described herein. Preferably, the biologically active portions of an IMI protein include one or more conserved domains selected from the group consisting of a Domain A, a Domain B, a Domain C, a Domain D and, a Domain E, wherein the conserved domain contains a mutation.

The invention also provides IMI chimeric or fusion polypeptides. As used herein, an IMI "chimeric polypeptide" or "fusion polypeptide" comprises an IMI polypeptide operatively linked to a non-IMI polypeptide. A "non-IMI polypeptide" refers to a polypeptide having an amino acid sequence that is not substantially identical to an IMI polypeptide, e.g., a polypeptide that is not an IMI isoenzyme, which peptide performs a different function than an IMI polypeptide. Within the fusion polypeptide, the term "operatively linked" is intended to indicate that the IMI polypeptide and the non-IMI polypeptide are fused to each other so that both sequences fulfill the proposed function attributed to the sequence used. The non-IMI polypeptide can be fused to the N-terminus or C-terminus of the IMI polypeptide. For example, in one embodiment, the fusion polypeptide is a GST-IMI fusion polypeptide in which the IMI sequence is fused to the C-terminus of the GST sequence. Such fusion polypeptides can facilitate the purification of recombinant IMI polypeptides. In another embodiment, the fusion polypeptide is an IMI polypeptide containing a heterologous signal sequence at its N-terminus. In certain host cells (e.g., mammalian host cells), expression and/or secretion of an IMI polypeptide can be increased through use of a heterologous signal sequence.

An isolated nucleic acid molecule encoding an IMI polypeptide having sequence identity to a polypeptide encoded by a polynucleotide sequence of SEQ ID NO:1 can be created by introducing one or more nucleotide substitutions, additions or deletions into a nucleotide sequence of SEQ ID NO:1 such that one or more amino acid substitutions, additions or deletions are introduced into the encoded polypeptide. Mutations can be introduced into a sequence of SEQ ID NO:1 by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an IMI polypeptide is preferably replaced with another amino acid residue from the same side chain family. Alternatively, in another embodiment, mutations can be introduced randomly along all or part of an IMI coding sequence, such as by saturation mutagenesis, and the resultant mutants can be screened for an IMI activity described herein to identify mutants that retain IMI activity. Following mutagenesis of the sequence of SEQ ID NO:1, the encoded polypeptide can be expressed recombinantly and the activity of the polypeptide can be determined by analyzing the imidazolinone resistance of a plant expressing the polypeptide as described in the Examples below.

To determine the percent sequence identity of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings.

It is to be understood that for the purposes of determining sequence identity, when comparing a DNA sequence to an RNA sequence, a thymidine nucleotide is equivalent to a uracil nucleotide. Preferably, the isolated IMI polypeptides included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence encoded by a nucleic acid comprising a polynucleotide sequence shown in SEQ ID NO:1. In another embodiment, the isolated IMI polypeptides included in the present invention are at least about 50-60%, preferably at least about 60-70%, and more preferably at leak about 70-75%, 75-80%, 80-85%, 85-90% or 90-95%, and most preferably at least about 96%, 97%, 98%, 99% or more identical to an entire amino acid sequence encoded by a nucleic acid comprising the polypeptide shown in SEQ ID NO:1.

Additionally, optimized IMI nucleic acids can be created. Preferably, an optimized IMI nucleic acid encodes an IMI polypeptide that modulates a plant's tolerance to imidazolinone herbicides, and more preferably increases a plant's tolerance to an imidazolinone herbicide upon its overexpression in the plant. As used herein, "optimized" refers to a nucleic acid that is genetically engineered to increase its expression in a given plant or animal. To provide plant optimized IMI nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) eliminate sequences that cause destabilization, inappropriate polyadenylation, degradation and termination of RNA, or that form secondary structure hairpins or RNA splice sites. Increased expression of IMI nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991 Proc. Natl. Acad. Sci. USA 88:3324-3328; and Murray et al., 1989 Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation 1A=n=1 Z $X_n-Y_n$ $X_n$ times 100 Z where $X_n$=frequency of usage for codon n in the host cell; $Y_n$=frequency of usage for codon n in the synthetic gene, n represents an individual codon that specifies an amino acid and the total number of codons is Z. The overall deviation of the frequency of codon usage, A, for all amino acids should preferably be less than about 25%, and more preferably less than about 10%.

Hence, an IMI nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized IMI nucleic acids of this invention also preferably have CG and. TA doublet avoidance indices closely approximating those of the chosen host plant (i.e., *Triticum monoccocum*). More preferably these indices deviate from that of the host by no more than about 10-15%.

In addition to the nucleic acid molecules encoding the IMI polypeptides described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense", for the purposes of the invention, refers to a nucleic acid comprising a polynucleotide that is sufficiently complementary to all or a portion of a gene, primary transcript or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide encoded by a nucleic acid comprising a polynucleotide sequence of SEQ ID NO:1.

In addition to the IMI nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of the sequence set forth in SEQ ID NO:1, an anti-sense sequence of the sequence set forth in SEQ ID NO:1, or naturally occurring mutants thereof. Primers based on a nucleotide sequence of SEQ ID NO:1 can be used in PCR reactions to clone IMI homologs. Probes based on the IMI nucleotide sequences can be used to detect transcripts or genomic sequences encoding the same or homologous polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an IMI polypeptide, such as by measuring a level of an IMI-encoding nucleic acid, in a sample of cells, e.g., detecting IMI mRNA levels or determining whether a genomic IMI gene has been mutated or deleted.

The invention further provides an isolated recombinant expression vector comprising an IMI nucleic acid as described above, wherein expression of the vector in a host cell results in increased resistance to an imidazolinone herbicide as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., IMI polypeptides, fusion polypeptides, etc.).

In a preferred embodiment of the present invention, the IMI polypeptides are expressed in plants and plants cells such as unicellular plant cells (such as algae) (see Falciatore et al., 1999 Marine Biotechnology 1(3):239-251 and references therein) and plant cells from higher plants (e.g., the spermatophytes, such as crop plants). An IMI polynucleotide may be "introduced" into a plant cell by any means, including transfection, transformation or transduction, electroporation, particle bombardment, agroinfection, biolistics and the like.

Suitable methods for transforming or transfecting host cells including plant cells can be found in Sambrook, et al. (Molecular Cloning: A Laboratory Manual, $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As increased resistance to imidazolinone herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crop plants are also preferred target plants for a genetic engineering as one further embodiment of the present invention. In a preferred embodiment, the plant is a wheat plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover.

In one embodiment of the present invention, transfection of an IMI polynucleotide into a plant is achieved by Agrobacterium mediated gene transfer. One transformation method known to those of skill in the art is the dipping of a flowering plant into an Agrobacteria solution, wherein the Agrobacteria contains the IMI nucleic acid, followed by breeding of the transformed gametes. Agrobacterium mediated plant transformation can be performed using for example the GV3101(pMP90) (Koncz and Schell, 1986 Mol. Gen. Genet. 204:383-396) or LBA4404 (Clontech) Agrobacterium tumefaciens strain. Transformation can be performed by standard transformation and regeneration techniques (Deblaere et al., 1994 Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-27314; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotica for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994 Plant Cell Report 13:282-285. Additionally, transformation of soybean can be performed using for example a technique described in European Patent No 0424 047, U.S. Pat. No. 5,322,783, European Patent No. 0397 687, U.S. Pat. Nos. 5,376,543 or 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

According to the present invention, the introduced IMI polynucleotide may be maintained in the plant cell stably if it is incorporated into a non-chromosomal autonomous replicon or integrated into the plant chromosomes. Alternatively, the introduced IMI polynucleotide may be present on an extra-chromosomal non-replicating vector and be transiently expressed or transiently active. In one embodiment, a homologous recombinant microorganism can be created wherein the IMI polynucleotide is integrated into a chromosome, a vector is prepared which contains at least a portion of an AHAS gene into which a deletion, addition or substitution has been introduced to thereby alter, e.g., functionally disrupt, the endogenous AHAS gene and to create an IMI gene. To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist 87(3):240-247). Other homologous recombination procedures in Triticum species are also well known in the art and are contemplated for use herein.

In the homologous recombination vector, the IMI gene can be flanked at its 5' and 3' ends by an additional nucleic acid molecule of the AHAS gene to allow for homologous recombination to occur between the exogenous IMI gene carried by the vector and an endogenous AHAS gene, in a microorganism or plant. The additional flanking AHAS nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95(8):4368-4373 for cDNA based recombination in *Physcomitrella patens*). However, since the IMI gene normally differs from the AHAS gene at very few amino acids, a flanking sequence is not always necessary. The homologous recombination vector is introduced into a microorganism or plant cell (e.g., via polyethylene glycol mediated DNA), and cells in which the introduced IMI gene has homologously recombined with the endogenous AHAS gene are selected using art-known techniques.

In another embodiment, recombinant microorganisms can be produced that contain selected systems that allow for regulated expression of the introduced gene. For example, inclusion of an IMI gene on a vector placing it under control of the lac operon permits expression of the IMI gene only in the presence of IPTG. Such regulatory systems are well known in the art.

Whether present in an extra-chromosomal non-replicating vector or a vector that is integrated into a chromosome, the IMI polynucleotide preferably resides in a plant expression cassette. A plant expression cassette preferably contains regulatory sequences capable of driving gene expression in plant cells that are operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof, but also all other terminators functionally active in plants are suitable. As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the polypeptide per RNA ratio (Gallie et al., 1987 Nucl. Acids Research 15:8693-8711). Examples of plant expression vectors include those detailed in: Becker, D. et al., 1992 New plant binary vectors with selectable markers located proximal to the left border, Plant Mol. Biol. 20:1195-1197; Bevan, M. W., 1984 Binary *Agrobacterium* vectors for plant transformation, Nucl. Acid Res. 12:8711-8721; and Vectors for Gene Transfer in Higher Plants; in Transgenic Plants, Vol. 1, Engineering and Utilization, eds.: Kung and R. Wu, Academic Press, 1993, S. 15-38.

Plant gene expression should be operably linked to an appropriate promoter conferring gene expression in a timely, cell or tissue specific manner. Promoters useful in the expression cassettes of the invention include any promoter that is capable of initiating transcription in a plant cell. Such promoters include, but are not limited to those that can be obtained from plants, plant viruses and bacteria that contain genes that are expressed in plants, such as *Agrobacterium* and *Rhizobium*.

The promoter may be constitutive, inducible, developmental stage-preferred, cell type-preferred, tissue-preferred or organ-preferred. Constitutive promoters are active under most conditions. Examples of constitutive promoters include the CaMV 19S and 35S promoters (Odell et al. 1985 Nature 313:810-812), the sX CaMV 35S promoter (Kay et al. 1987 Science 236:1299-1302) the Sep1 promoter, the rice actin promoter (McElroy et al. 1990 Plant Cell 2:163-171), the *Arabidopsis* actin promoter, the ubiquitan promoter (Christensen et al. 1989 Plant Molec. Biol. 18:675-689); pEmu (Last et al. 1991 Theor. Appl. Genet. 81:581-588), the figwort mosaic virus 35S promoter, the Smas promoter (Velten et al. 1984 EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock, the PPDK promoter is induced by light, the PR-1 promoter from tobacco, *Arabidopsis* and maize are inducible by infection with a pathogen, and the Adh1 promoter is induced by hypoxia and cold stress. Plant gene expression can also be facilitated via an inducible promoter (for review see Gatz, 1997 Annu. Rev. Plant Physiol. Plant Mol. Biol. 48:89-108). Chemically inducible promoters are especially suitable if time-specific gene expression is desired. Examples of such promoters are a salicylic acid inducible promoter (PCT Application No. WO 95/19443), a tetracycline inducible promoter (Gatz et al., 1.992 Plant J. 2:397-404) and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like. Seed preferred promoters are preferentially expressed during seed development and/or germination. For example, seed preferred prompters can be embryo-preferred, endosperm preferred and seed coat-preferred. See Thompson et al., 1989 BioEssays 10:108. Examples of seed preferred promoters include, but are not limited to cellulose synthase (celA), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP promoter from *Vicia faba* (Baeumlein et al., 1991 Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980) or the legumin B4 promoter (LeB4; Baeumlein et al., 1992 Plant Journal, 2(2):233-9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soy bean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546) and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985 Cell 43:729-736).

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an IMI polynucleotide can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) an IMI polynucleotide. Accordingly, the invention further provides methods for producing IMI polypeptides using the host cells of the invention. In one embodiment, the method comprises culturing the host cell of invention (into which a recombinant expression vector encoding an IMI polypeptide has been introduced, or into which genome has been introduced a gene encoding a wild-type or MI polypeptide) in a suitable medium until IMI polypeptide is produced. In another embodiment, the method further comprises isolating IMI polypeptides from the medium or the host cell. Another aspect of the invention pertains to isolated IMI polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of IMI polypeptide in which the polypeptide is separated from some of the cellular components of the cells in which it is naturally or recombinantly produced. In one embodiment, the language "substantially free of cellular material" includes preparations of an MI polypeptide having less than about 30% (by dry weight) of non-IMI material (also referred to herein as a "contaminating polypeptide"), more preferably less than about 20% of non-IMI material, still more preferably less than about 10% of non-IMI material, and most preferably less than about 5% non-IMI material.

When the IMI polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of IMI polypeptide in which the polypeptide is separated from chemical precursors or other chemicals that are involved in the synthesis of the polypeptide. In one embodiment, the language "substantially free of chemical precursors or other chemicals" includes preparations of an IMI polypeptide having less than about 30% (by dry weight) of chemical precursors or non-IMI chemicals, more preferably less than about 20% chemical precursors or non-IMI chemicals, still more preferably less than about 10% chemical precursors or non-IMI chemicals, and most preferably less than about 5% chemical precursors or non-IMI chemicals. In preferred embodiments, isolated polypeptides, or biologically active portions thereof, lack contaminating polypeptides from the same organism from which the IMI polypeptide is derived. Typically, such polypeptides are produced by recombinant expression of, for example, a *Triticum monococcum* IMI polypeptide in plants other than *Triticum monococcum* or microorganisms such as *C. glutamicum*, ciliates, algae or fungi.

The IMI polynucleotide and polypeptide sequences of the invention have a variety of uses. The nucleic acid and amino acid sequences of the present invention can be used to transform plants, thereby modulating the plant's resistance to imidazolinone herbicides. Accordingly, the invention provides a method of producing a transgenic plant having increased tolerance to an imidazolinone herbicide comprising, (a) transforming a plant cell with one or more expression vectors comprising one or more IMI nucleic acids, and (b) generating from the plant cell a transgenic plant with an increased resistance to an imidazolinone herbicide as compared to a wild type variety of the plant. In one embodiment, the multiple IMI nucleic acids are derived from different genomes. Also included in the present invention are methods of producing a transgenic plant having increased tolerance to an imidazolinone herbicide comprising, (a) transforming a plant cell with an expression vector comprising an IMI nucleic acid, wherein the nucleic acid is a non-Imi1 nucleic acid and (b) generating from the plant cell a transgenic plant with an increased resistance to an imidazolinone herbicide as compared to a wild type variety of the plant.

The present invention includes methods of modifying a plant's tolerance to an imidazolinone herbicide comprising modifying the expression of one or more IMI nucleic acids. Preferably, the nucleic acids are located on or derived from different genomes. The plant's resistance to the imidazolinone herbicide can be increased or decreased as achieved by increasing or decreasing the expression of an IMI polynucleotide, respectively. Preferably, the plant's resistance to the imidazolinone herbicide is increased by increasing expression of an IMI polynucleotide. Expression of an IMI polynucleotide can be modified by any method known to those of skill in the art. The methods of increasing expression of IMI polynucleotides can be used wherein the plant is either transgenic or not transgenic. In cases when the plant is transgenic, the plant can be transformed with a vector containing any of the above described IMI coding nucleic acids, or the plant can be transformed with a promoter that directs expression of endogenous IMI polynucleotides in the plant, for example. The invention provides that such a promoter can be tissue specific or developmentally regulated. Alternatively, non-transgenic plants can have endogenous IMI polynucleotide expression modified by inducing a native promoter. The expression of polynucleotides comprising SEQ ID NO:1 in target plants can be accomplished by, but is not limited to, one of the following examples: (a) constitutive promoter, (b) chemical-induced promoter, and (c) engineered promoter over-expression with for example zinc-finger derived transcription factors (Greisman and Pabo, 1997 Science 275:657).

In a preferred embodiment, transcription of the IMI polynucleotide is modulated using zinc-finger derived transcription factors (ZFPs) as described in Greisman and Pabo, 1997 Science 275:657 and manufactured by Sangamo Biosciences, Inc. These ZFPs comprise both a DNA recognition domain and a functional domain that causes activation or repression of a target nucleic acid such as an IMI nucleic acid. Therefore, activating and repressing ZFPs can be created that specifically recognize the IMI polynucleotide promoters described above and used to increase or decrease IMI polynucleotide expression in a plant, thereby modulating the herbicide resistance of the plant.

As described in more detail above, the plants produced by the methods of the present invention can be monocots or dicots. The plants can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example. In a preferred embodiment, the plant is a wheat plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover. In a preferred embodiment, the plant is a wheat plant. In each of the methods described above, the plant cell includes, but is not limited to, a protoplast, gamete producing cell, and a cell that regenerates into a whole plant. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations.

As described above, the present invention teaches compositions and methods for increasing the imidazolinone resistance of a wheat plant or seed as compared to a wild-type variety of the plant or seed. In a preferred embodiment, the imidazolinone resistance of a wheat plant or seed is increased such that the plant or seed can withstand an imidazolinone herbicide application of preferably approximately 10-400 g ai ha$^{-1}$, more preferably 20-160 g ai ha$^{-1}$, and most preferably 40-80 g ai ha$^{-1}$. As used herein, to "withstand" an imidazolinone herbicide application means that the plant is either not killed or not injured by such application.

Additionally provided herein is a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant, and wherein the plant comprises one or more IMI nucleic acids. In one embodiment, the plant comprises multiple IMI nucleic acids located on or derived from different genomes. In another embodiment, the plant comprises a non-Imi1 nucleic acid. By providing for wheat plants having increased resistance to imidazolinone, a wide variety of formulations can be employed for protecting wheat plants from weeds, so as to enhance plant growth and reduce competition for nutrients. An imidazolinone herbicide can be used by itself for pre-emergence, post-emergence, pre-planting and at-planting control of weeds in areas surrounding the wheat plants described herein or an imidazolinone herbicide formulation can be used that contains other additives. The imidazolinone herbicide can also be used as a seed treatment. Additives found in an imidazolinone herbicide formulation include other herbicides, detergents, adjuvants, spreading agents, sticking agents, stabilizing agents, or the like. The imidazolinone herbicide formulation can be a wet or dry preparation and can include, but is not limited to, flowable powders, emulsifiable concentrates and liquid concentrates. The imidazolinone herbicide and herbicide formulations can be applied in accordance with conventional methods, for example, by spraying, irrigation, dusting, or the like.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Mutagenesis and Selection of Resistant Wheat Lines

Approximately 15,000 seeds of the *Triticum monococcum* spring habit accession "TM23" was treated with EMS. The method used was: (1) presoak seed in water for four hours, (2) treat with 0.3% EMS for 16 hours, (3) rinse in water for 8 hours, (4) air-dry for four hours, and (5) plant the seed. Some of the harvested seed was further increased without selection for tolerance to imidazolinone herbicides. The harvested seed was planted and treated with 40 g/ha of imazamox. A total of 120 kg of seed was planted, resulting in approximately 2.4 million plants treated, assuming a kernel weight of 35 mg and 70% seedling emergence. The generation of seed screened ranged from M2 to M5, with over 72% of seed at least M3. Five plants were identified as tolerant, designated EM1 through EM5, and transplanted to a greenhouse for seed production. EM2 was increased under imidazolinone herbicide selection prior to initial field testing (Example 4).

Example 2

Transfer of EM2 from Diploid *Triticum Monococcum* to Hexaploid *T. Aestivum* ssp *Aestivum* and then to Tetraploid *T. Turgidum* ssp *Durum*

EMIMI is the designation of the *T. monococcum* EM2 source parent. Crocus is the designation of the *T. aestivum* ssp *aestivum* parent used. 605 florets of crocus were pollinated with EMIMI pollen, resulting in 84 $F_1$ seed. 38,409 florets of the $F_1$ plants were pollinated using Crocus pollen, resulting in 2 embryos which were embryo-rescued. The resultant $BC_1F_1$ plants were selfed to $BC_1F_2$ and treated with 20 g/ha of imazamox. Of the 24 plants so treated, 11 were fully resistant, 7 showed some injury, and 6 were susceptible. Resistant plants were crossed by the bread wheat variety Tea1, representing the $3^{rd}$ dose of bread wheat. Plants of the resultant line, with a pedigree of Crocus*2/EMIMI// CDC Tea1/3/ were crossed with either AC Elsa or AC Superb and coded respectively, 98PH8 (Elsa cross) and 98PH9 (Superb cross), 98PH8 was crossed an additional six times with AC Elsa and 98PH8 was crossed an additional six times with AC Superb. Two populations were coded as follows:

P00.35=98PH8/6*Elsa=Crocus*2/EM2//CDC Tea1/3/7*AC Elsa

P00.45=98PH9/6*Superb=Crocus*2/EM2//CDC Tea1/3/ 7*AC Superb.

Segregation of the backcross-derived plants in both populations fit an expected 1:1 tolerant:susceptible single gene model when treated with 20 g/h of imazamox. As expected with that rate and a single heterozygous tolerance gene in a bread wheat background, the plants scored as tolerant sustained some injury. Doubled haploids were produced from each population using the maize pollination method. Seven resistant DH lines were obtained from P00.35 and 78 resistant DH lines were obtained from P00.45. Those used in subsequent work have been shown to breed true for herbicide tolerance.

*T. aestivum* was used as the bridging species to transfer the EM2 gene from *T. monococcum* to *T. turgidum*. In each generation, plants were treated with at least a 20 g/h rate of imazamox prior to selecting plants as parents. An intermediate *T. aestivum* conversion with the pedigree "Crocus*2/ EM2//CDC Tea1/3/2*AC Superb" tolerant to imazamox was crossed by the *durum* line AC Avonlea. The resultant $F_1$ plants were selfed to produce an $F_2$ population, from which 52/390 plants were identified as resistant (no injury from herbicide application). Some of these were used as females and crossed by AC Avonlea. The resultant $BC_1F_1$ plants were again crossed by AC Avonlea. For the subsequent two generations, AC Avonlea was used as the female. The resultant line was designated 00DIMI#17 and had the pedigree: AC Avonlea*2/3/Crocus*2/EM2//CDC Tea1/3/2*AC Superb//3*AC Avonlea. This line was selfed to the F2, and F2 plants treated with 40 g/h of imazamox. Resistant F2 plants were advanced to the F4 generation. All 53 F4 plants tested survived application of 80 g/h imazamox. Across F4:5 lines, no susceptible plants were found out of the 124 plants treated with 80 g/h of imazamox, indicating stable insertion of the EM2 gene into a *durum* background.

Example 3

Results Regarding Inheritance of IMI Genes and Allelic. Relationships among IMI Genes In all the following discussion, the application rate of the imidazolinone herbicide imazamox that was used in the inheritance studies was 20 grams per hectare. This rate was sufficient to kill susceptible wheat plants. Parental material included is shown in FIG. 4.

During the introgression process, the EM2 gene segregated as expected for a single partially dominant gene. *Triticum monococcum* from which the EM2 mutation was derived is a diploid wheat containing only the A genome. Hexaploid wheat has the A genome as well as the B and D genome. Assuming that during introgression the EM2 gene was incorporated homologously into the A genome of hexaploid wheat as would be normally expected, then the EM2 mutation in parental materials "EM2" and "EM2FS4" described above would be on the A genome. The table below provides F2 segregation data that help elucidate allelic relationships among the various mutants. No parental material, with the exception of the susceptible line Tea1 had any susceptible plants when treated with imazamox; therefore, these data are not shown.

Lack of segregation in the $F_2$ generation indicates that parental lines share at least one allele at a particular locus. $F_2$ segregation ratios of 3:1, 15:1, and 63:1 indicate, respectively, one, two, and three independent loci. The segregation of 15A when crossed with the susceptible line Tea1 indicated two independent loci were involved with tolerance to imazamox (FIG. 5, Line 2). EM2 is at a different locus than FS4 (FIG. 5, Line 7). EM2 shares one locus with 15A (FIG. 5, Line 3). FS4 shares one locus with 15A (FIG. 5, Line 4). The EM2+FS4 parent crossed with 15A also did not segregate in the $F_2$ (FIG. 5, Line 5). FS4 appears to be on the D genome (Jim Anderson, personal communication). EM2 should be on the A genome. Therefore, the two loci involved with tolerance to imazamox in 15A should be on the A and D genomes. Parent 11A when crossed with the susceptible line Tea1 segregated as a single locus (FIG. 5, Line 1). It was independent of the tolerance locus in EM2 (FIG. 5, Line 6) and FS4 (FIG. 5, Line 9). As would be expected from the lack of segregation of EM2 and FS4 with 15A, 11A was also independent of the loci in 15A (FIG. 5, Line 10) and the EM2+FS4 parent (FIG. 5, Line 8). Assuming that the AHAS genes are in a homologous set in hexaploid wheat, there are only three expressed AHAS genes, and each of the expressed genes are on a different genome, then 11A should be on the B genome.

Example 4

Tolerance to IMI Herbicides Provided by EM2 in Einkorn, *Durum*, and Hexaploid Wheat, and Increased Tolerance when Combined with Other Non-Allelic Tolerance Genes The EM2 line tolerant to imazamox (Example 1) was evaluated at a single field location for various agronomic characteristics that could be affected by herbicide injury. Data from the three years of evaluation are shown in FIG. 6. The 1998 data are means of two replications. Yield data from 1999 and 2000 are means of four replications. The other data from 1999 are means of two replications. The Einkorn check was susceptible to 40 grams of imazamox, all plants dying. The EM2 mutation in Einkorn background conferred excellent tolerance to the 40 g/ha rate.

The EM2 line was evaluated for overall crop injury at three rates of imazamox, three times during the growing season. These data are presented in FIG. 7. In 1999, only slight injury was seen initially, and symptoms gradually disappeared over the course of the season. In 2000, no injury was observed in the EM2 line, while the non-herbicide tolerant check was virtually killed.

The tolerance conferred by EM2 in *durum* (tetraploid) and bread wheat (hexaploid) backgrounds has also been demonstrated. The breeding history of the lines tested was previously described (Example 2). As indicated in Example 2, when $F_{4:5}$ lines of the EM2 *durum* recovery 00DIMI#17 were evaluated for tolerance to 80 g/h of imazamox, all plants were tolerant, while all plants of the susceptible *durum* line used as a check were killed, indicating that EM2 confers tolerance to the Imi class of herbicides in a *durum* background. The doubled haploid derived line P00.45, composed of EM2 in a hexaploid background, was tolerant to 20 g/ha imazamox as a parental check in allelism studies described in Example 3; all plants of the susceptible hexaploid check were killed at that rate.

The combination of more than one Imi-tolerance gene has been demonstrated to increase tolerance of wheat to imidazolinone herbicides. Four genotypes were tested for tolerance to two different rates of imazamox. Genotypes included an FS4 only line, BW755; Tea1 15A, previously described as having two independent loci for tolerance to Imi-herbicides; a double-haploid derived line of EM2+FS4, and a line derived from the cross of 15A and 11A, through conventional bulk selection of the most tolerant plants over successive generations at increasing rates of imazamox. Rates of imazamox included 200 and 600 grams per hectare. Seedling injury of the 18 to 25 plants per treatment per genotype was rated on a per plant basis using five categories ranging from death to no injury. The data are summarized in FIG. 8.

No plants were killed at either rate. The single gene line, BW755, containing FS4, was injured at both rates. Previous research has indicated that 11A and FS4 provide similar tolerance in bread wheat. The two two-gene lines, Tea 1 15A and EM2/FS4 reacted similarly. No injury occurred at the lower rate, demonstrating increased tolerance over the one gene plant, but all were injured at the higher rate. The three gene line was still segregating, as evidenced by some plants exhibiting injury at both rates, but approximately half the plants had no injury at the highest rate, demonstrating increased tolerance over either of the two gene lines.

I claim:

1. A wheat plant, wherein the plant is obtained by a process comprising crossing a wheat plant of line Einkorn IMI, a representative sample of seed of the line having been deposited with ATCC under Patent Deposit Designation Number PTA-4113, with another *Triticum* line, wherein the plant obtained by the process comprises an IMI polypeptide comprising a serine to asparagine substitution in Domain E, said IMI polypeptide encoded by an Imi3 nucleic acid, wherein the Imi3 nucleic acid is the AHAS gene of the A-genome of the wheat plant, and said plant having increased tolerance to an imidazolinone herbicide as compared to that of a wild type variety of the plant.

2. The wheat plant of claim 1, wherein the Imi3 nucleic acid comprises the polynucleotide sequence set forth in SEQ ID NO: 1.

3. The wheat plant of claim 1, wherein the imidazolinone herbicide comprises at least one of: imazethapyr, imazapic, imazamox, imazaquin, imazethabenz, imazapyr, a mixture of imazapyr and imazamox.

4. The wheat plant of claim 1, wherein the imidazolinone herbicide comprises imazethapyr.

5. The wheat plant of claim 1, wherein the imidazolinone herbicide comprises imazamox.

6. A plant part of a wheat plant of claim 1, wherein the plant part comprises the Imi3 nucleic acid.

7. A plant cell of a wheat plant of claim 1, wherein the plant cell comprises the Imi3 nucleic acid.

8. A seed produced by a wheat plant of claim 1, wherein the seed is true breeding for an increased resistance to an imidazolinone herbicide as compared to a wild type variety of the wheat plant seed.

9. The wheat plant of claim 1, wherein the plant is not transgenic.

10. A wheat plant comprising multiple Imi nucleic acids from different wheat genomes, wherein the wheat plant is obtained by a process comprising crossing a wheat plant of line Einkorn IMI, a representative sample of seed of the line having been deposited with ATCC under Patent Deposit Designation Number PTA-4113, with another *Triticum* line, wherein the plant obtained by the process comprises a first Imi nucleic acid of the multiple Imi nucleic acids, wherein the first Imi nucleic acid is an Imi3 nucleic acid that encodes an IMI polypeptide comprising a serine to asparagine substitution in Domain E, the Imi3 nucleic acid being the AHAS gene of the A-genome of the wheat plant, and said plant having increased tolerance to an imidazolinone herbicide as compared to that of a wild type variety of the plant.

11. The wheat plant of claim 10, wherein the Imi3 nucleic acid comprises the polynucleotide sequence set forth in SEQ ID NO:1.

12. The wheat plant of claim 10, wherein a second Imi nucleic acid of the multiple Imi nucleic acids is selected from the group consisting of Imi1 nucleic acids and Imi2 nucleic acids.

13. The wheat plant of claim 10, wherein each of the multiple IMI nucleic acids encode an IMI protein independently comprising a mutation in a conserved amino acid sequence selected from the group consisting of a Domain A, a Domain B, a Domain C, a Domain D, and Domain E.

14. The wheat plant of claim 10, comprising two IMI nucleic acids.

15. The wheat plant of claim 10, comprising three IMI nucleic acids.

16. The wheat plant of claim 10, wherein the plant is non-transgenic.

17. The wheat plant of claim 10, wherein the imidazolinone herbicide comprises at least one of: imazethapyr, imazapic, imazamox, imazaquin, imazethabenz, imazapyr, a mixture of imazapyr and imazamox.

18. The wheat plant of claim 10, wherein the imidazolinone herbicide comprises imazethapyr.

19. The wheat plant of claim 10, wherein the imidazolinone herbicide comprises imazamox.

20. A plant part of a wheat plant of claim 10, wherein the plant part comprises the Imi3 nucleic acid.

21. A plant cell of a wheat plant of claim 10, wherein the plant cell comprises the Imi3 nucleic acid.

22. A seed produced by a wheat plant of claim 10, wherein the seed is true breeding for an increased resistance to an imidazolinone herbicide as compared to a wild type variety of the wheat plant seed.

23. A method of controlling weeds in the vicinity of wheat plants comprising:
  a. providing the plant of claim 1 or claim 10; and
  b. applying an imidazolinone herbicide to the weeds and to the wheat plant.

24. The plant of claim 1 or claim 10, wherein said plant exhibits tolerance to 60 g/ha imazamox.

25. The plant of claim 1 or claim 10, wherein said plant exhibits tolerance to 200 g/ha imazamox.

26. The seed of claim 8 or claim 22, wherein the seed further comprises a seed treatment.

27. The seed of claim 26, wherein the seed treatment comprises an imidazolinone herbicide.

28. The seed of claim 27, wherein the imidazolinone herbicide comprises at least one of: imazapyr, imazethapyr, imazapic, imazamox, imazaquin, or imazethabenz.

29. A method for identifying the presence of an Imi3 nucleic acid in a plant, plant part, cell or seed thereof, comprising:

(a) providing a plant, plant part, cell, or seed of the plant of claim 1 or claim 10;
(b) extracting nucleic acid material from said plant, plant part, cell or seed;
(c) assaying the extracted nucleic acid material for the presence of the Imi3 nucleic acid, wherein said Imi3 nucleic acid comprises:
   a nucleic acid comprising the polynucleotide sequence of SEQ ID NO:1.

* * * * *

SEQUENCE LISTING

<160> NUMBER OF SEQ ID NOS: 8

<210> SEQ ID NO 1
<211> LENGTH: 370
<212> TYPE: DNA
<213> ORGANISM: Triticum sp.

<400> SEQUENCE: 1

```
gatggtagtt tcctcatgaa cattcaggag ttggcgttga tccgtattga gaacctccca      60
gtgaaggtga tgatattgaa caaccagcat ctgggaatgg tggtgcagtg ggaggatagg     120
ttttacaagg ccaaccgggc acacacatac cttggcaacc cagaaaatga gagtgagata     180
tatccagatt ttgtgacgat tgctaaagga ttcaacgttc cggcagttcg tgtgacgaag     240
aagagcgaag tcactgcagc aatcaagaag atgcttgaga ccccagggcc atacttgttg     300
gatatcattg tcccgcatca ggagcacgtg ctgcctatga tcccaaacgg aggtgctttt     360
aaggacatga                                                            370
```

<210> SEQ ID NO 2
<211> LENGTH: 370
<212> TYPE: DNA
<213> ORGANISM: Triticum sp.

<400> SEQUENCE: 2

```
gatggtagtt tcctcatgaa cattcaggag ttggcgttga tccgtattga gaacctccca      60
gtgaaggtga tgatattgaa caaccagcat ctgggaatgg tggtgcagtg ggaggatagg     120
ttttacaagg ccaaccgggc acacacatac cttggcaacc cagaaaatga gagtgagata     180
tatccagatt ttgtgacgat tgctaaagga ttcaacgttc cggcagttcg tgtgacgaag     240
aagagcgaag tcactgcagc aatcaagaag atgcttgaga ccccagggcc atacttgttg     300
gatatcattg tcccgcatca ggagcacgtg ctgcctatga tcccaagcgg aggtgctttt     360
aaggacatga                                                            370
```

<210> SEQ ID NO 3
<211> LENGTH: 370
<212> TYPE: DNA
<213> ORGANISM: Artificial Sequence
<220> FEATURE:
<223> OTHER INFORMATION: Description of Artificial Sequence: Consensus sequence
<220> FEATURE:
<221> NAME/KEY: modified_base
<222> LOCATION: (347)
<223> OTHER INFORMATION: a, t, c or g

<400> SEQUENCE: 3
gatggtagtt tcctcatgaa cattcaggag ttggcgttga tccgtattga gaacctccca    60
gtgaaggtga tgatattgaa caaccagcat ctgggaatgg tggtgcagtg ggaggatagg   120
ttttacaagg ccaaccgggc acacacatac cttggcaacc cagaaaatga gagtgagata   180
tatccagatt tgtgtacgat tgctaaagga ttcaacgttc cggcagttcg tgtgacgaag   240
aagagcgaag tcactgcagc aatcaagaag atgcttgaga ccccagggcc atacttgttg   300
gatatcattg tcccgcatca ggagcacgtg ctgcctatga tcccaancgg aggtgctttt   360
aaggacatga                                                          370

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 4

Ala Ile Thr Gly Gln Val Pro Arg Arg Met Ile Gly Thr
  1               5                  10

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 5

Gln Trp Glu Asp
  1

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 6

Val Phe Ala Tyr Pro Gly Gly Ala Ser Met Glu Ile His Gln Ala Leu
  1               5                  10                  15

Thr Arg Ser

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 7

Ala Phe Gln Glu Thr Pro
  1               5

```
<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 8

Ile Pro Ser Gly Gly
 1               5
```